United States Patent
Andtsjo et al.

(10) Patent No.: US 8,758,573 B2
(45) Date of Patent: Jun. 24, 2014

(54) REMOVAL OF HYDROCARBONS FROM AN AQUEOUS STREAM

(75) Inventors: Henrik Andtsjo, Porvoo (FI); Maarit Aarni-Sirvio, Helsinki (FI)

(73) Assignee: Borealis Technology Oy, Ponvoo (FI)

(*) Notice: Subject to any disclaimer, the term of this patent is extended or adjusted under 35 U.S.C. 154(b) by 455 days.

(21) Appl. No.: 12/808,368

(22) PCT Filed: Dec. 22, 2008

(86) PCT No.: PCT/EP2008/011006
§ 371 (c)(1),
(2), (4) Date: Jul. 26, 2010

(87) PCT Pub. No.: WO2009/080339
PCT Pub. Date: Jul. 2, 2009

(65) Prior Publication Data
US 2010/0282591 A1    Nov. 11, 2010

(30) Foreign Application Priority Data

Dec. 20, 2007   (EP) .................................. 07150221

(51) Int. Cl.
| | | |
|---|---|---|
| C02F 1/04 | (2006.01) | |
| B01D 3/34 | (2006.01) | |
| C07C 39/04 | (2006.01) | |
| B01D 17/02 | (2006.01) | |

(52) U.S. Cl.
USPC ............ 203/10; 203/14; 203/18; 203/21; 203/35; 203/78; 203/80; 203/DIG. 25; 210/513; 210/774; 210/806; 568/749

(58) Field of Classification Search
USPC ........... 203/10, 14, 18, 21, 31, 35, 43–44, 78, 203/80, DIG. 25; 210/513, 774, 806; 568/749
See application file for complete search history.

(56) References Cited

U.S. PATENT DOCUMENTS 4,298,765 A * 11/1981 Cochran et al. ................. 203/6
4,374,283 A    2/1983 Aneja
(Continued)

FOREIGN PATENT DOCUMENTS

| DE | 1042599 | 11/1958 |
|---|---|---|
| EP | 505146 | 9/1992 |
| EP | 571042 | 5/1993 |
| EP | 0717024 A1 | 6/1996 |
| EP | 758636 | 2/1997 |

(Continued)

OTHER PUBLICATIONS

R.T. P. Pinto, et. al., Title: Strategies for Recovering Phenol From Wastewater: Thermodynamic Evaluation and Environmental Concerns, Fluid Phase Equilibria, vol. 228-229, Oct. 22, 2004, pp. 447-457.

*Primary Examiner* — Virginia Manoharan
(74) *Attorney, Agent, or Firm* — Sutherland Asbill & Brennan LLP

(57) ABSTRACT

The present application concerns a process for the removal of hydrocarbons from an aqueous stream, which process may include conducting a phenol-containing water stream into a separation column, separating the phenol-containing water in the column using heat to form an overhead portion and a bottoms portion, and collecting the overhead portion as well as the bottoms portion. Further, the process may include adding an eluent to an aqueous stream, thereby forming an aqueous mixture, subsequently conducting the aqueous mixture into a separation vessel, wherein it is allowed to settle into two phases, which form a hydrocarbon stream and a phenol-containing water stream, subsequently collecting the hydrocarbon stream, and conducting the phenol-containing water stream to the separation column for further separation.

11 Claims, 1 Drawing Sheet

(56) References Cited

U.S. PATENT DOCUMENTS

| | | | |
|---|---|---|---|
| 5,414,154 | A | 5/1995 | Jenczewski et al. |
| 5,811,598 | A * | 9/1998 | Alessi et al. ............... 568/754 |
| 6,071,409 | A | 6/2000 | Bondy et al. |
| 2002/0066661 | A1* | 6/2002 | Schwarz et al. ............ 202/154 |
| 2003/0221948 | A1* | 12/2003 | Bortolo et al. ............... 203/43 |
| 2004/0236152 | A1* | 11/2004 | Black et al. ................. 568/414 |
| 2005/0034970 | A1* | 2/2005 | Schwarz et al. ............. 203/22 |
| 2005/0240065 | A1* | 10/2005 | Blaschke et al. ........... 568/810 |

FOREIGN PATENT DOCUMENTS

| | | |
|---|---|---|
| EP | 1256561 A1 | 11/2002 |
| GB | 707173 | 4/1954 |
| GB | 1426606 | 3/1976 |
| WO | 02/102751 A2 | 12/2002 |
| WO | 2004/046039 | 6/2004 |
| WO | 2005/102936 | 11/2005 |
| WO | 2005/102974 A1 | 11/2005 |
| WO | 2009/080340 | 7/2009 |

\* cited by examiner

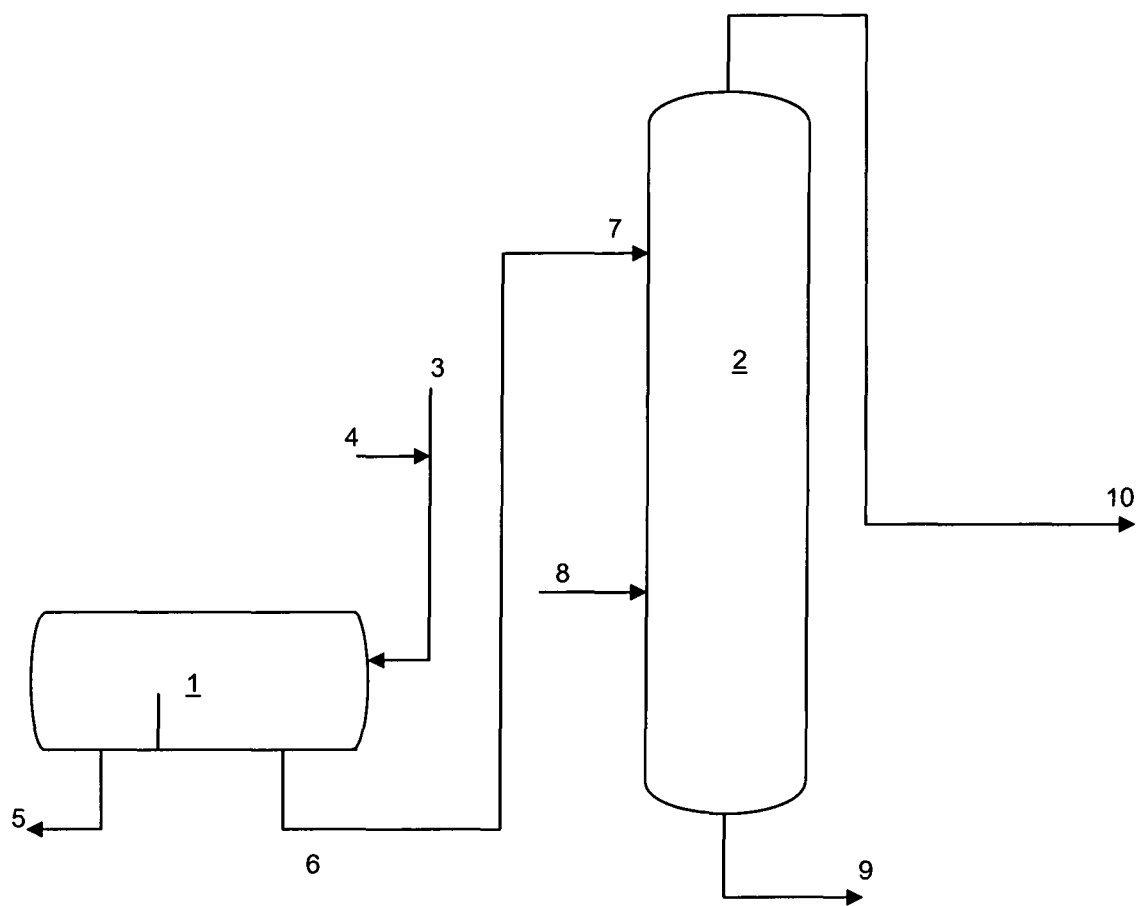

REMOVAL OF HYDROCARBONS FROM AN AQUEOUS STREAM

RELATED APPLICATIONS

The present application is a section 371 application related to International Application No. PCT/EP2008/011006, filed on Dec. 22, 2008, which, in turn, claims priority to EP 07150221.5, filed on Dec. 20, 2007.

FIELD OF THE INVENTION

The present invention concerns a process and an apparatus for the removal of hydrocarbons from an aqueous stream. Preferably, this process and apparatus is used to separate hydrocarbons from an aqueous stream obtained from a phenol production process. The process also allows the formation of an aqueous stream with very low phenol content and an aqueous stream containing phenol which can be recycled back into a phenol production process to maximize yield.

DESCRIPTION OF RELATED ART

Phenol is commonly manufactured through a process in which cumene is oxidized to cumene hydroperoxide (CHP) and the resulting oxidation product mixture is concentrated and subjected to an acid catalyzed cleavage reaction. Subsequently, the cleavage product mixture is neutralized and conducted to a distillation section, wherein the main products of the cleavage reaction, i.e. phenol and acetone, are first separated and then purified through a series of distillation steps or other purification steps.

The reaction starting from cumene is summarized below:

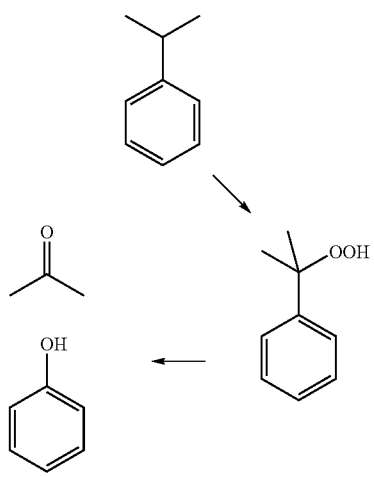

Of course, the phenol production process does not proceed with 100% efficiency so as well as the desired end products there will be other impurities present at the end of the cleavage reaction. These might be unreacted starting materials such as cumene, or CHP or side products produced during the rearrangement reaction that takes place as the hydroperoxide breaks down. Such compounds include methyl styrene, acetophenone residues, mesityl oxide and 2-methylbenzofuranone.

The cleavage product mixture obtained in the mentioned cleavage reaction is acidic due to the presence of the acid catalyst. When neutralizing this acid, an aqueous solution containing an alkaline component is generally used so the neutralized cleavage product reaction mixture contains an aqueous phase which needs to be purified. Whilst the majority of the desired compounds and impurities are present in the organic layer which forms after neutralization and are hence readily separated from this aqueous phase, the aqueous phase still contains unacceptable amounts of hydrocarbon products and this needs to be purified.

In fact, in other parts of the phenol production process, aqueous streams are produced that will contain amounts of hydrocarbons such as phenol and the impurities mentioned above. For example, water obtained during washing steps or from washing equipment which is used to contain hydrocarbons might need purification.

It is not acceptable to release water containing high levels of impurity into waste water systems. Moreover, it is uneconomic to treat water having high levels of phenol as this compound is a valuable resource and as much as possible should be recovered. Moreover, the inventors have found that the levels of hydrocarbons in the waste water are so high that the aqueous mixture should not simply be distilled as high amounts of hydrocarbons in the aqueous stream going to the dephenolation column (separation column) may cause fouling of e.g. trays and pre-heaters, whereby these surfaces need to be cleaned repeatedly. The inventors therefore sought new ways of removing hydrocarbons from aqueous streams and ultimately the producing an aqueous waste water stream in which the phenol content is very low.

Many prior art documents such as US2005/0240065 teach the use of ethers or ketones as extraction solvents for phenol. These documents are concerned only with phenol removal however and not with the removal of other hydrocarbons which might also be present and which are not soluble in ethers. U.S. Pat. No. 4,374,283 teaches the use of methylsiobutyl ketone as a extraction solvent for phenol and U.S. Pat. No. 6,071,409 teaches the use of alkyl tertiary amyl ether. The idea here is that the phenol dissolves in the ether or ketone which partitions from the water phase thereby allowing easy separation of the phenol and water. There is a cost implication with using ethers or ketones however as these compounds are not available at a typically phenol production plant and have to be brought in. There is also the issue of what to do with the ether or ketone that enters the water phase. This is therefore a less than ideal solution.

The prior art processes generally employ a single step to remove phenol from water, typically a single extraction step. The inventors have found that often a single extraction step is not enough to remove all phenol when using a readily available extractant.

SUMMARY OF THE INVENTION

It is an aim of the present invention to provide an efficient process for removing hydrocarbons from an aqueous stream.

Particularly, it is an aim of the present invention to provide a two-step process for removing hydrocarbons from an aqueous stream, wherein a first portion of the hydrocarbons (typically hydrocarbons comprising C and H only) is removed in a first step and a second portion of the hydrocarbons (typically phenol) is removed in a second step.

These and other objects, together with the advantages thereof over known processes and apparatuses, are achieved by the present invention, as hereinafter described and claimed.

The present invention concerns a process for the removal of hydrocarbons from an aqueous stream, which process comprises a first phase separation stage followed by conducting a phenol-containing water stream into a separation column, separating the phenol-containing water in the column using heat to form an overhead portion and a bottoms portion, and collecting the overhead portion as well as the bottoms portion.

Further, the present invention concerns an apparatus for separating an organic phase and an aqueous phase and for carrying out the distillation.

More specifically, the process of the present invention comprises the removal of hydrocarbons from an aqueous stream, which process comprises
- adding an eluent to an aqueous stream comprising hydrocarbons (including phenol) to thereby form an aqueous mixture,
- allowing the aqueous mixture to settle into two phases, which form a hydrocarbon stream and a phenol-containing water stream,
- subsequently collecting the hydrocarbon stream,
- conducting a phenol-containing water stream into a separation column (2),
- separating the phenol-containing water in the column using heat into an overhead portion and a bottoms portion, and
- collecting the overhead portion as well as the bottoms portion.

Preferably the invention comprises
- adding an eluent to an aqueous stream comprising hydrocarbons to thereby form an aqueous mixture,
- subsequently conducting the aqueous mixture into a separation vessel (1), wherein it is allowed to settle into two phases, which form a hydrocarbon stream and a phenol-containing water stream,
- subsequently collecting the hydrocarbon stream,
- conducting a phenol-containing water stream into a separation column (2),
- separating the phenol-containing water in the column using heat into an overhead portion and a bottoms portion, and collecting the overhead portion as well as the bottoms portion.

Further, the apparatus of the present invention is characterized by what is stated in the characterizing clause of the apparatus claim and the use of the present invention is characterized by what is stated in the use claims.

The present invention provides a two-step process for the removal of hydrocarbons from aqueous streams, in particular for the removal of phenol production impurities and phenol to leave an aqueous component which can be released to waste treatment. In the first step, a first portion of hydrocarbons is removed from an aqueous stream comprising those hydrocarbons. That step obviously decreases the load to the second step where further hydrocarbons are recovered and a purer water stream produced. The second step is preferably carried out in a distillation column, and the decreased load gives a significantly cleaner column and a faster phenol separation process. In particular, the impurities removed in the first step of the process are ones which cause fouling in the second step and hence the use of the first step is essential.

Furthermore, when used in a phenol production process, the present invention provides phenol and acetone products with a higher purity compared to a production procedure with a simpler dephenolation process or no dephenolation process at all.

BRIEF DESCRIPTION OF THE DRAWING

FIG. 1 is a schematic drawing of the apparatus of the present invention.

DETAILED DESCRIPTION OF THE PREFERRED EMBODIMENTS OF THE INVENTION

The present invention requires the presence of a hydrocarbon containing aqueous stream which needs purification. The amount of hydrocarbons in the aqueous stream, before the addition of eluent, is generally about 2 to 15 wt %, preferably 4 to 10 wt %, especially 5 to 8 wt %. Alternatively, the amount may be 2-7 w-%, preferably 3-5 w-%, most preferably 3.5-4 w-%. The aqueous stream will typically contain two or more hydrocarbons (e.g. phenol and another hydrocarbon such as cumene or other impurities from the cleavage reaction of CHP such as AMS, mesityl oxide etc). The major hydrocarbon present will however be phenol, e.g. 80 wt % or more, such as 90 wt % or more of the hydrocarbons in the aqueous stream will be phenol.

The level of phenol in any waste water stream which is to be discharged to the sewers must be very low, e.g. less than 1 ppm however the inventors have realized that the cheapest way of ensuring such low levels of phenol in water is by the use of a bioreactor to treat waste water. The present inventors realized therefore that the extraction procedures before the bioreactor are preferably such that the phenol content is reduced to a level that the bacteria in the bioreactor can handle and that any impurity that might poison the bacteria, such as some heavy hydrocarbons, is removed. These hydrocarbons also cause problems in the distillation of phenolic water and should be removed for that reason too. Whilst it is obviously beneficial to recover as much phenol as possible from the water, there is a trade off between the cost of phenol recovery and the amount of phenol recovered. The inventors have found that water with levels of phenol of less than 250 ppm, such as 100 ppm to 250 ppm, e.g. around 200 ppm can be transferred to the bioreactor and these levels also offer the phenol producer excellent levels of phenol recovery without onerously expensive recovery procedures.

The aqueous stream to be purified according to the invention preferably derives from a part of a phenol production plant, e.g. it is the aqueous phase which is separated off after neutralization of the cleavage products.

In the first step of the process of the invention, an eluent is added to a hydrocarbon containing aqueous stream to form an aqueous mixture.

In the context of the hydrocarbons in the aqueous stream in the present invention, the term hydrocarbon is intended to cover not only compounds such as cumene formed exclusively from carbon and hydrogen but also other compounds which may be side products of the cumene process such as some ketones, aldehydes or hydroxylated compounds. The term hydrocarbon also includes phenol in this context. It is an essential feature of this invention that phenol is present in the aqueous stream to be purified. The aqueous stream should also contain one or more further organic or inorganic components, e.g. cumene or sodium phenate. Ideally the aqueous stream will contain at least one hydrocarbon selected from cumene, AMS, 2-methylbenzofuran, mesityloxide or benzaldehyde. The term "aqueous mixture" is intended to mean a hydrocarbon containing aqueous stream further containing an amount of added eluent. In a preferred embodiment during the elution step hydrocarbons other than phenol are extracted into the organic phase leaving the majority of the phenol in the aqueous phase.

The eluent used is preferably a hydrocarbon containing only carbon and hydrogen atoms. It should preferably not be an ether or a ketone or comprise an ether or a ketone. Some prior art processes employ ethers/ketones as extraction solvents to encourage phenol out of the aqueous stream. These processes in general do not seek to recover phenol which is the main aim of the present process. The present invention does not seek to remove phenol from the aqueous stream using the eluent extraction step. Phenol is primarily separated from water in the second step of the invention. In the first step, the present inventors have found that hydrocarbons are a better choice of eluent as they encourage better phase separation and are also able to remove other hydrocarbon impurities from the aqueous stream more easily than ethers and ketones. There is also a cost implication of using an ether or ketone. The ether for extraction would need to be purchased and transported to the phenol plant and that is a large expense. The present inventors ideally employ cumene as an extraction solvent as cumene is already readily available as it is the compound used to form phenol. Ideally therefore the eluent is a compound which is readily available at the phenol plant, ideally cumene or benzene, especially cumene.

The purpose of the addition of eluent is to create a sufficient density difference between the organic phase and the aqueous phase for their separation. Hydrocarbons which contain carbon and hydrogen only are essentially insoluble in water so make an ideal extraction solvent here.

The amount of eluent, preferably cumene added is sufficient to give an aqueous mixture with an eluent concentration of 0.2 to 10 wt %, e.g. 0.5 to 5 wt %, especially about 1 wt %. It is within the scope of the invention for the amount added to be 1-40 w-%, preferably 5-20 w-%, before separation. Overall therefore the hydrocarbon fraction of the aqueous mixture may be, for example 3 to 47 wt %, especially 3 to 16 wt %.

The eluent is preferably the only material added to the aqueous stream (other than an acid as discussed below). The aqueous stream of the invention is preferably free of sodium carbonate, for example.

The aqueous mixture is conducted, if necessary, into a separation vessel, wherein it is allowed to settle into two phases. One phase (typically the upper phase) is a hydrocarbon phase and can form a hydrocarbon stream and the second phase (typically the lower phase) is a phenol containing aqueous phase and can form a phenol-containing aqueous stream. The hydrocarbon stream can be collected and the phenol-containing aqueous stream conducted to the separation column for further separation.

When separating the aqueous mixture into two phases, it divides into a "hydrocarbon stream", i.e., the organic phase of the separated aqueous mixture, and a "phenol-containing aqueous stream", i.e., the aqueous phase of the separated aqueous mixture, containing water and at least a portion of phenol.

Some phenol will however be removed from the aqueous mixture in the hydrocarbon layer and should be recovered to maximize yield. It is therefore preferred if the hydrocarbon stream is taken for further heavies recovery where any phenol and eluent can be recovered and recycled to appropriate parts of the phenol production process. The phenol recovered can be transferred to phenol purification and the cumene either to be used again as an eluent or to the start of the whole process for use as a reactant.

There is still too much phenol in the aqueous layer to be discharged into the waste water systems, typically a bioreactor. Moreover, there is still a significant amount of residual phenol which is a valuable commercial resource and should be recovered.

The conditions prevailing in the separation vessel 1 are preferably close to atmospheric conditions, the temperature being, for example, 30-50° C., preferably about 40° C., and the pressure being 110-200 kPa. It is preferred if the temperature is below the boiling point of any volatile fractions in the hydrocarbon portion.

According to a preferred embodiment of the present invention, the pH of the aqueous stream being conducted to the separation vessel 1 is maintained at a level of 4.5-6 using an acid, preferably an inorganic acid, most preferably sulfuric acid. In this way, any sodium phenate in the aqueous stream is converted to phenol and sodium salt. A lower pH than the mentioned level may cause equipment corrosion. The concentration of salt in the aqueous stream depends on the treatments that are carried out on the stream before conducting it to the vessel 1. However, the salt concentration ($Na^+$ and $K^+$ ions) should not be allowed to increase above 1000 ppm.

According to a preferred embodiment of the present invention, the mentioned separation process is used as a part of phenol production, whereby the separated organic phase contains the eluent, while the aqueous phase contains residual phenol and water.

The hydrocarbon phase can be separated into its constituent parts by distillation and the eluent used recycled back to the start of the process. If the eluent is cumene, this can be returned for oxidation to CHP. Some fractions of the hydrocarbon phase can be transferred to others parts of the phenol production plant for maximization of phenol output.

The phenol-containing aqueous stream is conducted into a separation column where the phenol-containing aqueous stream in the column is separated using heat to form an overhead portion and a bottoms portion. Both the overhead portion as well as the bottoms portion can them be collected.

In the context of the present invention, the term "distillation" is intended to mean a method for separating chemical components based on the differences in their volatilities. The phenol containing aqueous stream conducted to the separation column (i.e. distillation column) is separated into two distillates, i.e., an overhead portion, containing "light" or "low-boiling" components, i.e., components that vaporize under the conditions prevailing in the column, and an unevaporated fraction, i.e., a bottoms portion, containing "heavy" or "high-boiling" components, i.e., components that remain in liquid form under the conditions prevailing in the column. The identities of the compounds included in the heavy components or in the light components depend on the prevailing conditions in the distillation column, such as the temperature and the pressure. The term "evaporation" is intended to mean any process where at least a portion of a mixture of components is converted from a liquid phase to a vapor phase, generally by heating.

The process and the apparatus of the present invention may be used to separate hydrocarbons from any aqueous stream containing phenol. Preferably, the apparatus of the invention is arranged downstream from the cumene hydroperoxide cleavage section of a phenol production process. The phenol production process typically comprises process steps wherein phenol and acetone are produced through the oxidation of cumene to cumene hydroperoxide (CHP) and the subsequent steps of concentrating the CHP, cleaving the CHP into phenol, acetone and other cleavage products, neutralizing, washing and desalting the cleavage products and finally separating the acetone from the phenol and purifying both desired products.

The aqueous stream to be processed according to the present invention preferably results from this mentioned process. Ideally in such a process a cumene feed and an air feed required for the mentioned oxidation are washed, for example using a caustic solution, i.e., a solution having a pH of 8-12, to ensure a sufficient grade of purity. Subsequently, the cumene is subjected to oxidation using air or concentrated oxygen as the mentioned air feed, the concentrated oxygen being a gaseous mixture containing up to 100% oxygen, preferably about 22-80% oxygen, the rest being mostly inert gases. The concentration of the CHP formed during the oxidation is increased, after which the CHP is subjected to a cleavage process. The resulting cleavage product mixture is subsequently neutralized and subjected to desalting. Finally, the aqueous phase from the desalting process is conducted to a stripper column, wherein the organic components contained therein are recovered.

The function of the distillation column, when being a part of a phenol production procedure, is based on the fact that phenol and water form an azeotrope, which has a boiling point below that of water and phenol. As water is in excess in the aqueous stream at this point, any left over phenol can be removed from the excess water as part of the azeotrope using stripping. The azeotrope also has the characteristic that its relative volatility in comparison with water increases as the pressure increases.

According to an embodiment of the present invention, the conditions in the separation column are maintained at levels that give an overhead portion that consists of a concentration of 75-99 w-%, preferably 85-95 w-%, most preferably about 90 w-%, of the mentioned azeotrope. The concentration of phenol in the overhead portion under these conditions is about 3-10 w-%, preferably about 5-8 w-%.

As almost all the phenol is removed overhead with water, the bottoms portion in the distillation column contains very low amounts of phenol and gives rise to water which can be discharged to waste treatment e.g. in a bioreactor. The phenol concentration in the bottoms fraction can be about 50-250 ppm, preferably about 100-225 ppm. In addition to the small amount of phenol in the bottoms portion, it contains mostly water.

According to a preferred embodiment of the present invention, the separation column is a distillation column operated with reflux using recycled steam of a temperature around 100-200° C., preferably about 150° C. The pressure in the column is preferably maintained close to atmospheric pressure, preferably slightly above atmospheric pressure, more preferably at about 110–300 kPa.

The overhead column contains valuable amounts of phenol and can be recycled to an appropriate part of the phenol production process. In particular, the phenol water azeotrope can be recycled to the cleavage step where both water and phenol are present anyway.

The apparatus of the present invention for removing hydrocarbons from an aqueous stream preferably contains the following parts (FIG. 1)

1 separation vessel
2 separation column

The separation vessel 1 further comprises the following parts:

3 aqueous mixture inlet
4 eluent inlet
5 hydrocarbon outlet
6 aqueous outlet

The separation column 2 further comprises the following parts:

7 aqueous inlet
8 steam inlet
9 bottoms outlet
10 overhead outlet

Thus, according to the present invention, the apparatus for the removal of hydrocarbons from an aqueous stream comprises a separation column 2 for separating a phenol-containing aqueous stream into a bottoms portion and an overhead portion, as well as a separation vessel 1 positioned upstream from the separation column 2, which vessel 1 is in fluid communication with the column 2. In vessel 1, an aqueous mixture may be allowed to settle into two phases, which form a hydrocarbon stream and a phenol-containing aqueous stream.

The separation vessel 1 comprises an inlet 3 for the aqueous stream and an inlet 4 for the eluent as well as an outlet 5 for hydrocarbons and an outlet 6 for the phenol-containing aqueous stream. Likewise, the separation column 2 comprises an inlet 7 for the phenol-containing aqueous stream, which inlet 7 is connected to the aqueous outlet 6 on the separation vessel 1, a steam inlet 8, an outlet 9 for the bottoms portion and an outlet 10 for the overhead portion.

EXAMPLE 1

Cumene (1 wt %) is added to an aqueous stream comprising phenol and alpha methylstyrene (10 wt % in total). The pH of the aqueous mixture is adjusted to 5 by the addition of sulphuric acid. The organic and aqueous layers are allowed to separate at ambient temperature and pressure.

The aqueous layer is removed. The aqueous layer is transferred to a distillation apparatus and heated under reflux at 150° C. The overhead fraction is collected and found to contain 10% phenol and 90% water. The bottoms fraction contains water and only very minor levels of phenol of around 200 ppm.

It should be apparent that the foregoing relates only to the preferred embodiments of the present application and that numerous changes and modification may be made herein by one of ordinary skill in the art without departing from the general spirit and scope of the invention as defined by the following claims and the equivalents thereof.

We claim:

1. A process for the removal of hydrocarbons from an aqueous stream, which process comprises:
    adding 0.5 to 5 wt % cumene as an eluent to an aqueous stream comprising 2 to 15 wt % of hydrocarbons comprising phenol and at least one alpha methyl styrene or mesityl oxide to thereby form an aqueous mixture,
    allowing the aqueous mixture to settle into two phases, which form a hydrocarbon stream containing said at least one alpha methyl styrene or mesityl oxide and a water stream comprising the majority of the phenol,
    subsequently collecting the hydrocarbon stream and passing the collected hydrocarbon stream to distillation for recovery,
    conducting the phenol-containing water stream into a separation column,
    separating the phenol-containing water in the column using heat into an overhead portion and a bottoms portion, and
    collecting the overhead portion as well as the bottoms portion, and
    transferring the bottoms portion to a bio waste water treatment reactor and recycling the overhead portion for phenol recovery.

2. A process as claimed in claim 1, which process comprises:
    conducting the aqueous mixture formed by adding the eluent to the aqueous stream into a separation vessel, wherein it is allowed to settle into the hydrocarbon stream and the phenol-containing water stream.

3. The process of claim 2, wherein the temperature in the separation vessel is 30-50° C. and the pressure is 110-200 kPa.

4. The process of claim 2, wherein the separation column is operated with reflux using recycled steam at a temperature of 100-200° C.

5. The process of claim 2, wherein the temperature in the separation vessel is at about 40° C. and the pressure is about 110-200 kPa.

6. The process of claim 2, wherein the separation column is operated with reflux using recycled steam at a temperature of about 150° C.

7. The process of claim 1, wherein the pH of the aqueous stream during the process is maintained at 4.5-6.

8. The process of claim 1, wherein a concentration of salt in the aqueous stream is below 1000 ppm.

9. The process of claim 1, wherein the amount of added eluent is sufficient to give an eluent concentration of 0.5 to 5 wt % before separation.

10. The process of claim 1, wherein the pressure of the separation vessel is about 110-2001 kPa.

11. The process of claim 1, wherein the pH of the aqueous stream during the process is maintained using sulphuric acid.

* * * * *